(12) United States Patent
Davenport et al.

(10) Patent No.: US 7,814,915 B2
(45) Date of Patent: Oct. 19, 2010

(54) AESTHETIC TREATMENT FOR WRINKLE REDUCTION AND REJUVENATION

(75) Inventors: Scott A. Davenport, Half Moon Bay, CA (US); David A. Gollnick, San Francisco, CA (US); Steven Christensen, Fremont, CA (US); Dean A. MacFarland, Magnolia, MA (US); Robert Bernhard Estrada, San Carlos, CA (US)

(73) Assignee: Cutera, Inc., Brisbane, CA (US)

( * ) Notice: Subject to any disclaimer, the term of this patent is extended or adjusted under 35 U.S.C. 154(b) by 0 days.

(21) Appl. No.: 11/681,700

(22) Filed: Mar. 2, 2007

(65) Prior Publication Data
US 2007/0265604 A1 Nov. 15, 2007

Related U.S. Application Data

(60) Provisional application No. 60/778,896, filed on Mar. 3, 2006, provisional application No. 60/888,061, filed on Feb. 2, 2007.

(51) Int. Cl.
*A61B 19/00* (2006.01)
*A61B 18/20* (2006.01)

(52) U.S. Cl. .............. 128/898; 606/3; 606/9; 607/89

(58) Field of Classification Search ............ 606/3, 606/9, 10; 607/88, 89; 128/898
See application file for complete search history.

(56) References Cited

U.S. PATENT DOCUMENTS

| | | | | |
|---|---|---|---|---|
| 5,546,214 A | 8/1996 | Black et al. | ................. | 359/203 |
| 5,558,667 A | 9/1996 | Yarborough et al. | ........... | 606/9 |
| 5,642,370 A | 6/1997 | Mitchell et al. | ............... | 372/25 |
| 5,643,252 A * | 7/1997 | Waner et al. | .................... | 606/9 |
| 5,741,247 A | 4/1998 | Rizoiu et al. | .................. | 606/10 |
| 5,743,902 A | 4/1998 | Trost | ........................... | 606/18 |
| 5,785,521 A | 7/1998 | Rizoiu et al. | .................. | 433/29 |
| 5,957,915 A | 9/1999 | Trost | ........................... | 606/13 |
| 5,964,749 A | 10/1999 | Eckhouse et al. | .............. | 606/9 |
| 5,968,037 A | 10/1999 | Rizoiu et al. | .................. | 606/13 |
| 6,074,382 A * | 6/2000 | Asah et al. | ..................... | 606/9 |
| 6,080,148 A | 6/2000 | Damasco et al. | ............. | 606/10 |
| 6,090,102 A * | 7/2000 | Telfair et al. | .................. | 606/10 |
| 6,096,031 A | 8/2000 | Mitchell et al. | ............... | 606/15 |
| 6,174,325 B1 | 1/2001 | Eckhouse | .................... | 607/88 |
| 6,231,567 B1 | 5/2001 | Rizoiu et al. | .................. | 606/10 |
| 6,254,597 B1 | 7/2001 | Rizoiu et al. | .................. | 606/13 |

(Continued)

OTHER PUBLICATIONS

C. Apel et al., "The Ablation Threshold of Er:YAG and Er:YSGG Laser Radiation in Dental Enamel," *Laser Med. Sci.* (2002), vol. 17, pp. 246-252.

(Continued)

*Primary Examiner*—Ahmed M Farah
(74) *Attorney, Agent, or Firm*—Morrison & Foerster LLP

(57) ABSTRACT

A dermatological treatment method includes directing laser energy having a wavelength of 2.79 µm onto skin. According to disclosed methods, the energy can function to ablate a first portion of epidermal tissue, coagulate an underlying second portion of epidermal tissue, and promote collagen formation in tissue of the underlying dermis. In an exemplary treatment apparatus, a laser using a YSGG gain medium is mounted in a handpiece. The handpiece may include a two-axis scanner to allow for uniform scanning of the energy over the tissue surface.

10 Claims, 8 Drawing Sheets

U.S. PATENT DOCUMENTS

| | | | |
|---|---|---|---|
| 6,288,499 B1 | 9/2001 | Rizoiu et al. | 315/200 A |
| 6,328,733 B1 | 12/2001 | Trost | 606/13 |
| 6,350,123 B1 | 2/2002 | Rizoiu et al. | 433/80 |
| 6,350,261 B1 * | 2/2002 | Domankevitz et al. | 606/17 |
| 6,425,873 B1 * | 7/2002 | Marchitto et al. | 600/573 |
| 6,544,256 B1 | 4/2003 | Rizoiu et al. | 606/13 |
| 6,561,803 B1 | 5/2003 | Rizoiu et al. | 433/80 |
| 6,567,582 B1 | 5/2003 | Rizoiu et al. | 385/25 |
| 6,575,964 B1 | 6/2003 | Hobart et al. | 606/10 |
| 6,610,053 B1 | 8/2003 | Rizoiu et al. | 606/13 |
| 6,706,035 B2 * | 3/2004 | Cense et al. | 606/9 |
| 6,744,790 B1 | 6/2004 | Tilleman et al. | 372/12 |
| 6,813,302 B1 | 11/2004 | Stoneman et al. | 372/75 |
| 6,821,272 B2 | 11/2004 | Rizoiu et al. | 606/2 |
| 6,887,233 B2 | 5/2005 | Angeley et al. | 606/17 |
| 6,942,658 B1 | 9/2005 | Rizoiu et al. | 606/16 |
| 6,951,558 B2 | 10/2005 | Angeley et al. | 606/18 |
| 6,976,984 B2 * | 12/2005 | Cense et al. | 606/9 |
| 7,060,061 B2 * | 6/2006 | Altshuler et al. | 606/3 |
| 7,108,690 B1 * | 9/2006 | Lefki et al. | 606/10 |
| 7,108,693 B2 | 9/2006 | Rizoiu et al. | 606/15 |
| 7,187,822 B2 | 3/2007 | Rizoiu et al. | 385/25 |
| 2001/0016732 A1 | 8/2001 | Hobart et al. | 606/2 |
| 2002/0169442 A1 * | 11/2002 | Neev | 606/9 |
| 2003/0199859 A1 * | 10/2003 | Altshuler et al. | 606/9 |
| 2004/0034341 A1 * | 2/2004 | Altshuler et al. | 606/3 |
| 2005/0247321 A1 | 11/2005 | Waner et al. | 128/898 |
| 2005/0256517 A1 | 11/2005 | Boutoussov | 606/16 |
| 2006/0276776 A1 | 12/2006 | Lin | 606/5 |
| 2007/0016176 A1 | 1/2007 | Boutoussov et al. | 606/17 |
| 2008/0172047 A1 * | 7/2008 | Altshuler et al. | 606/9 |

OTHER PUBLICATIONS

R.P. Gailitis et al., "Comparison of Laser Phacovaporization Using the Er-YAG and the Er-YSGG Laser," *Arch. Ophthalmol.*, vol. 111, May 1993, pp. 697-700.

E.D. Jansen et al., "Temperature Dependence of the Absorption Coefficient of Water for Midinfrared Laser Radiation," *Lasers in Surgery and Medicine* (1994), vol. 14, pp. 258-268.

R. Kaufmann et al., "Cutting and Skin-Ablative Properties of Pulsed Mid-Infrared Laser Surgery," *J. Dermatol. Surg. Oncol.* (1994), vol. 20, pp. 112-118.

J. Meister et al., "Influence of the water content in dental enamel and dentin on ablation with erbium YAG and erbium YSGG lasers," *Journal of Biomedical Optics,* vol. 11, No. 3, May/Jun. 2006, pp. 034030-1-034030-7.

V. Pavelec et al., "Use of Er, Cr:YSGG Versus Standard Lasers in Laser Assisted Uvulopalatoplasty for Treatment of Snoring," *Laryngoscope,* vol. 116, Aug. 2006, p. 1512.

C.J. Walinski, "Irritation fibroma removal: A comparison of two laser wavelengths," *General Dentistry,* May/Jun. 2004, pp. 236-238.

O. Kermani, et al., "Q-Switched CTE:YAG Laser Ablation: Basic Investigations on Soft (Corneal) and Hard (Dental) Tissues," *Lasers in Surgery and* Medicine (1993), vol. 13, pp. 537-542.

* cited by examiner

AESTHETIC TREATMENT FOR WRINKLE REDUCTION AND REJUVENATION

RELATED APPLICATIONS

This application claims the benefit of U.S. Provisional Application No. 60/778,896, filed Mar. 3, 2006, U.S. Provisional Application No. 60/888,061, filed Feb. 2, 2007.
—Inventors: Scott A. Davenport, David A. Gollnick, Steven Christensen, Dean A. MacFarland and Robert Bernhard Estrada—

FIELD OF THE INVENTION

The subject invention relates to a dermatological treatment method and apparatus using laser energy for resurfacing and/or rejuvenating skin.

BACKGROUND

Ablative skin resurfacing has been performed using carbon dioxide lasers emitting radiation at 10.6 microns. (See for example, U.S. Pat. No. 5,335,242) While these lasers could provide good results, recovery times were long. The long recovery times have been attributed to the significant depth of thermal damage associated with this longer wavelength radiation.

In an effort to reduce recovery time, Er:YAG lasers, operating at an output wavelength of 2.94 µm, have been used to ablate tissue. The very high water absorption associated with the 2.94 µm wavelength decreased thermal damage and decreased recovery times, although a reduction in efficacy was sometimes observed. Generally, this reduction in efficacy is thought to be a consequence of a reduced thermal damage profile in skin, post-ablation. An example of the use of Er:YAG lasers for tissue treatment can be found in U.S. Pat. No. 6,395,000 which utilizes high repetition rate pulses (greater than 100 hertz). Another approach is to treat the tissue with micropulses within a relatively long pulse envelope. See U.S. Patent Applications 2001/0016732 and 2004/0133190. See also U.S. Pat. No. 6,193,711. All of these patent documents are incorporated by reference.

The approach described herein is intended to both increase efficacy and reduce recovery time.

DETAILED DESCRIPTION

Figure 1A:
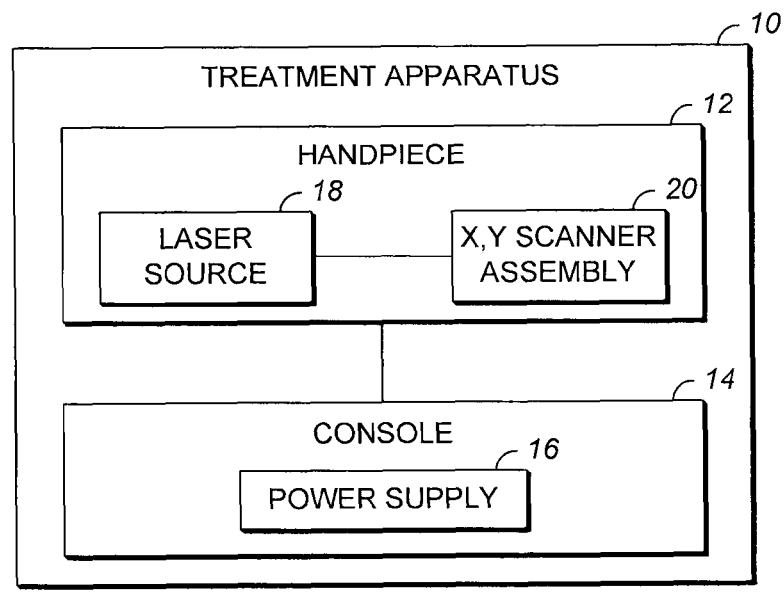
FIG. 1A is a schematic block diagram illustrating a dermatological treatment apparatus of the type disclosed herein.

Referring to FIG. 1A, in an exemplary embodiment of a treatment apparatus 10 includes a handpiece 12 coupled to a treatment console 14 housing a power supply 16. Power supply 16 may be a high voltage power supply of the type provided by Cutera, Inc. (Brisbane Calif.) in consoles for use with its Nd:YAG laser product line, and in particular any of the power supplies used with the CoolGlide family of lasers (CoolGlide CV, CoolGlide Excel, and CoolGlide Vantage), or with the CoolGlide Xeo, Xeo SA and Solera Opus consoles.

Laser source 18 is provided with an Er:YSGG or a Cr,Er:YSGG gain medium. This gain medium has a primary output at 2.79 µm which has a depth of coagulation in skin that falls between the depths associated with $CO_2$ lasers (wavelength=10.6 µm) and Er:YAG lasers (wavelength=2.94 µm.). The characteristic depth of coagulation in skin after laser ablation is 40 µm for 2.94 µm light, 75 µm for 2.79 µm light and 125 µm for 10.60 µm light (Kaufmann et al J Dermatol Surg Oncol 1994;20:112-118). As discussed in greater detail below, use of a primary wavelength of 2.79 µm ablates to remove a precise amount of tissue, while also coagulating to create a natural dressing and to promote new collagen formation.

A laser based on an Er:YSGG or Cr,Er:YSGG gain medium offers two other advantages. First, it is more efficient than Er:YAG. Second, the upper level lifetime is ten times longer, allowing low threshold operation allowing longer pulse durations relative to Er:YAG lasers at similar energy levels. Longer pulse durations may be exploited to produce different post-ablation thermal damage profiles in treated skin. In exemplary modes of operation, pulse durations on the order of 0.2 to 25 ms and preferably 0.5 to 10 ms are contemplated, with spot sizes on the order of between 1 and 10 mm, repetition rates ranging from single shots to 20 Hz, and preferred fluences within the range of 0.25 and 20 $J/cm^2$.

As shown in FIG. 1A, in the exemplary embodiment, laser source 18 is integrated into the handpiece 12. Integrating the laser components (e.g. monolithic laser rod resonator, excitation flash lamp, cooling features) and associated power detectors, optical components etc. into the handpiece avoids the problems of delivering the light from the console to the tissue. Thus, light can be delivered directly to the target tissue directly from the handpiece without having to pass through an articulated arm or fiber optic element. As discussed in greater detail below, the handpiece preferably includes a two-axis scanner 20 operable to uniformly scan the beam of light across the tissue surface to produce a two-dimensional treatment pattern on the skin.

Figure 1B:
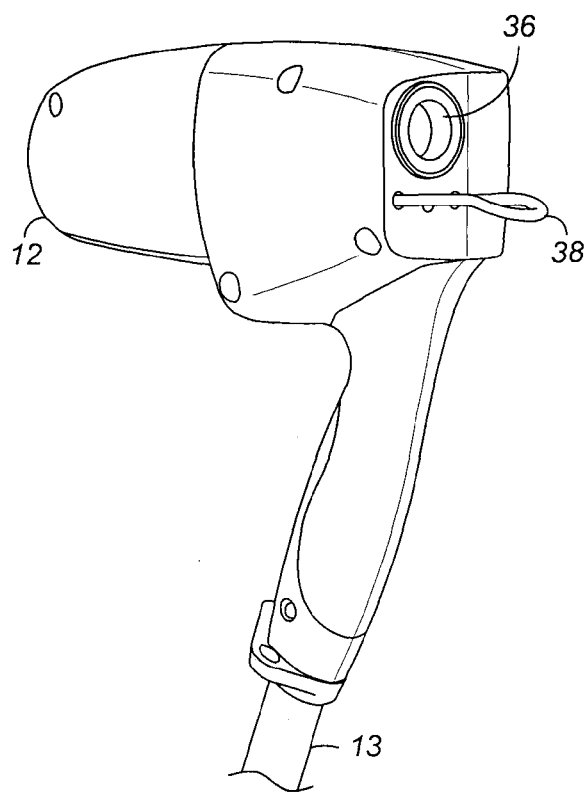
FIG. 1B is a perspective view of a handpiece of the apparatus of FIG. 1A.

The handpiece 12 is illustrated in FIG. 1B. Handpiece includes an umbilical cable 13 that houses electrical cables to provide power from the power supply to drive the flash lamp and scanner motors, to provide a signal path for detector signals, encoders, serial communication, a memory device that identifies the handpiece, and a supply and return water line (to remove heat generated by the flash lamp). The proximal end of the umbilical cable is semi-permanently attached to the laser system console and the distal end is permanently attached to the body of the delivery hand piece. An activation switch (not shown) such as a foot pedal is provided for use in initiating and terminating treatment.

Figure 2:
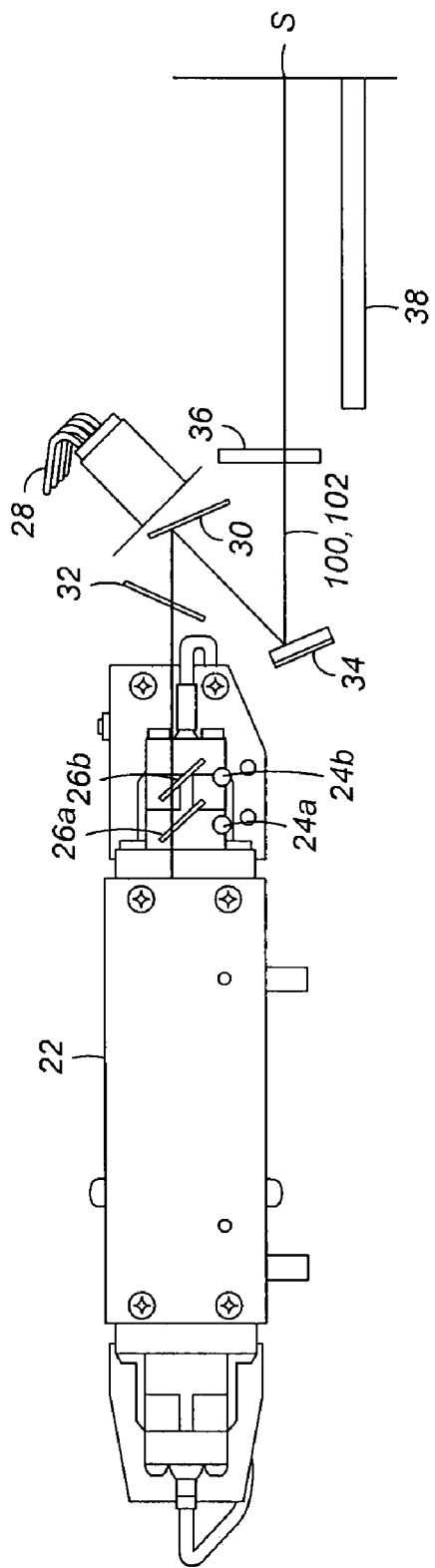
FIG. 2 is an optical schematic illustrating optical components within the handpiece of FIG. 1A.

FIG. 2 schematically illustrates the optical components within the handpiece. As shown, the handpiece includes a laser resonator cavity 22 containing the excitation flash lamp, laser crystal and associated mirrors. A portion of the beam 100 exiting the laser cavity 100 is diverted to a pair of photodetectors 24a, 24b by a pair of independent beam splitters 26a, 26b for use in monitoring output power. An aiming diode 28 generates an aiming beam of light 102. Beam combining mirror 30 combines the beam 100 from the laser 18 with the aiming beam 102 so that the aiming beam is parallel and coincident with the treatment beam. During use, the aiming beam shows the user where the energy from the laser is impinging on the skin.

A safety shutter 32 is positioned between the laser cavity 22 and the combining mirror 30. The shutter has open and closed positions. When the shutter is in the open position the beam 100 passes to the next optical component, which in FIG. 2 is the combining mirror 30. In the closed position, the beam 100 is deflected into a beam dump (not shown).

When not directed to the beam dump, the beam 100 impinges onto X-Y scanning mirror 34 which is driven by stepper motors to provide X-Y movement of the beam 100 on skin S. A protective window 36 on the handpiece (see also FIG. 1B) protects the internal optical components. A distance guide 38, which may be stainless steel, sets the distance between the handpiece 12 and the target treatment site. During use, the distance guide is placed in direct contact with the patient's skin.

Figure 3:
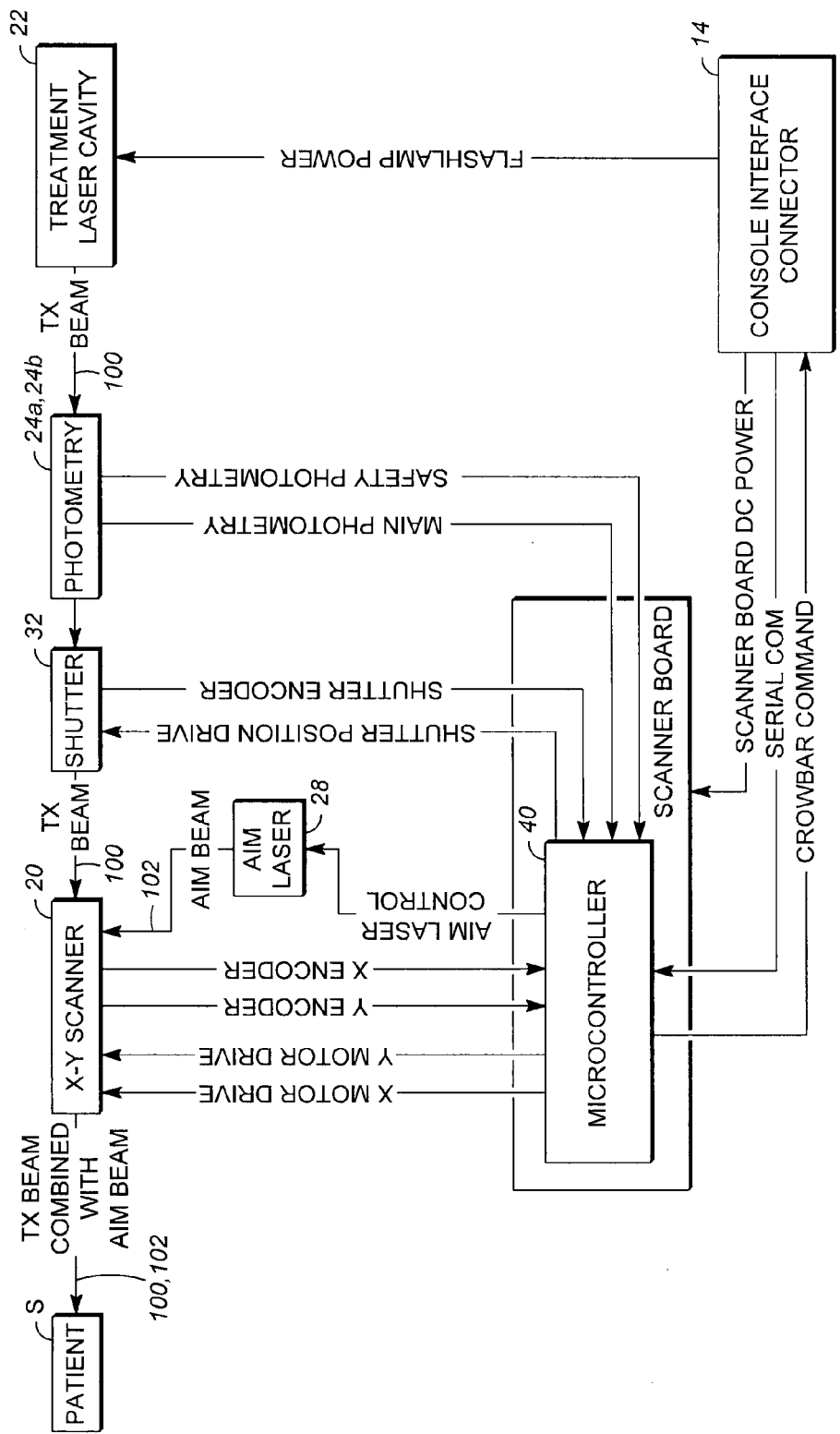
FIG. 3 is a schematic block diagram illustrating basic control electronics and associated components of the treatments apparatus of FIG. 1A.

Control electronics are schematically illustrated in FIG. 3. Independent signals from photodetectors 24a, 24b are received by microcontroller 40, which uses the input to monitor and regulate laser power. The photodetectors utilize detector circuits that are independent from each other and that use no shared components. This ensures that no single component failure lead to generation of inaccurate readings by both detectors. This avoids delivery of improper levels laser treatment energy to the patient.

Microcontroller 40 additionally provides drive signals to the stepper motors of the X,Y scanner 20. Encoders associated with X and Y direction stepper motors provide feedback for use by the microcontroller in identifying the rotational positions of the stepper motor shafts.

As discussed, safety shutter 32 is positioned to terminate delivery of the treatment beam to the patient S. An encoder attached to the shaft of the shutter motor detects the position of the safety shutter. The microcontroller 40 monitors the position of the safety shutter 32 and in the event of a discrepancy can terminate laser exposure by closing the safety shutter. Others ways of terminating exposure include disabling the high voltage power supply to prevent charging of the main charging capacitor or disabling the discharge of the main charging capacitor (thus preventing the firing of the flash lamp).

Details of the X,Y scanner assembly 20 will next be discussed in connection with FIGS. 4-7B. In general, the X,Y scanner 20 is operable to move the scanning mirror 34 (FIG. 2) in two orthogonal directions to produce a pattern of treated regions on the skin.

Figure 4:
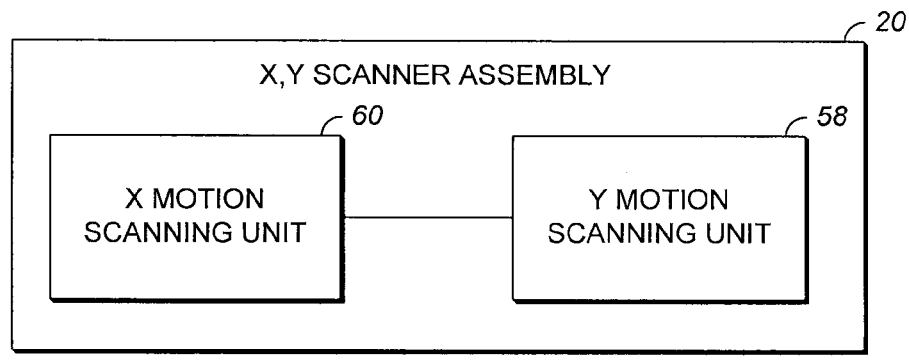
FIG. 4 is a high level block diagram schematically illustrating components of the X,Y scanner assembly of the treatment apparatus of FIG. 1A.

Referring to FIG. 4, the scanner 20 includes an x-motion scanning unit 60 for scanning the light across the tissue surface in a first direction (arbitrarily labeled the "x" direction), and a y-motion scanning unit 58 for moving the light in a second direction that is preferably orthogonal to the x-direction. Although various scanner configurations may be used for this purpose, one suitable scanner uses a pair of stepper motors operable to move a single mirror relative to two axes. This scanner is differentiated from prior scanners in part for its single moving mirror design, use of stepper motors for precise movement and miniature size.

Figure 5:
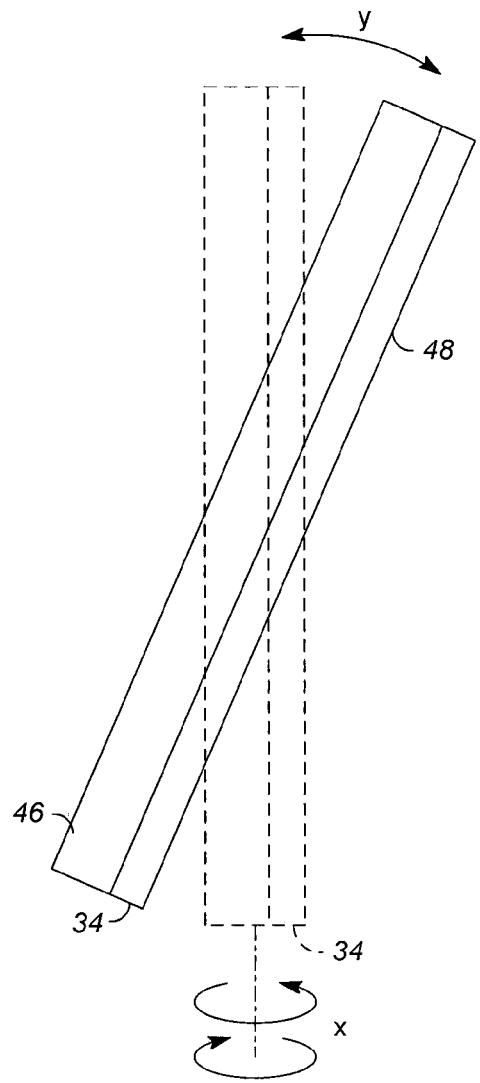
FIG. 5 schematically illustrates X and Y scanning movement of the mirror mount supporting the mirror shown in the optical schematic of FIG. 2.

FIG. 5 shows a side view of scanning mirror 34 mounted on a rectangular mirror mount 46. Mount 46 is attached to the face of mirror 34 that is opposite to the reflective surface 48 used by the mirror to reflect laser light onto tissue. This figure schematically illustrates general movement of the mirror and mount during scanning. One direction of movement, referred to here as y-direction movement, involves using a first stepper motor to pivot the mount in a forward and backward direction as indicated by arrows "y". The second form of movement, referred to here as the x-direction movement, involves using a second stepper motor to pivot the mount laterally as indicated by arrows "x".

Figure 6B:
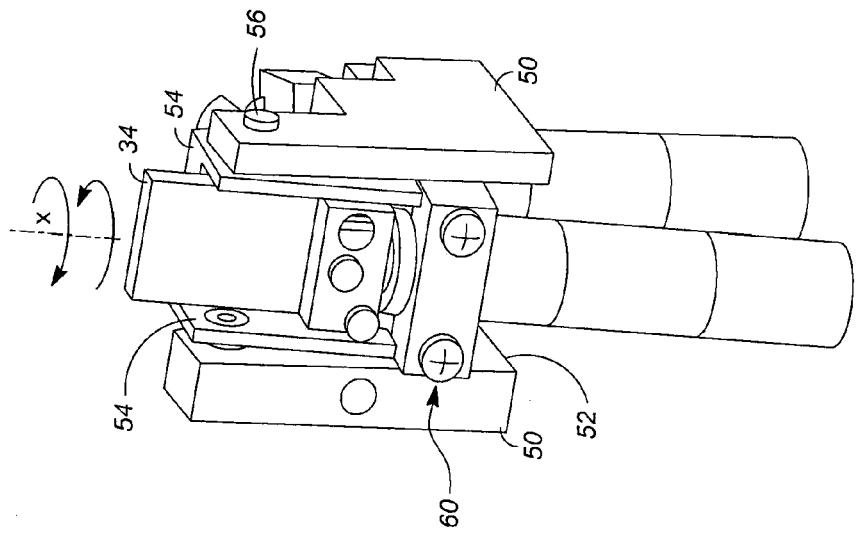
FIG. 6B is a front perspective view of the X,Y scanning assembly of FIG. 6A.
Figure 6A:
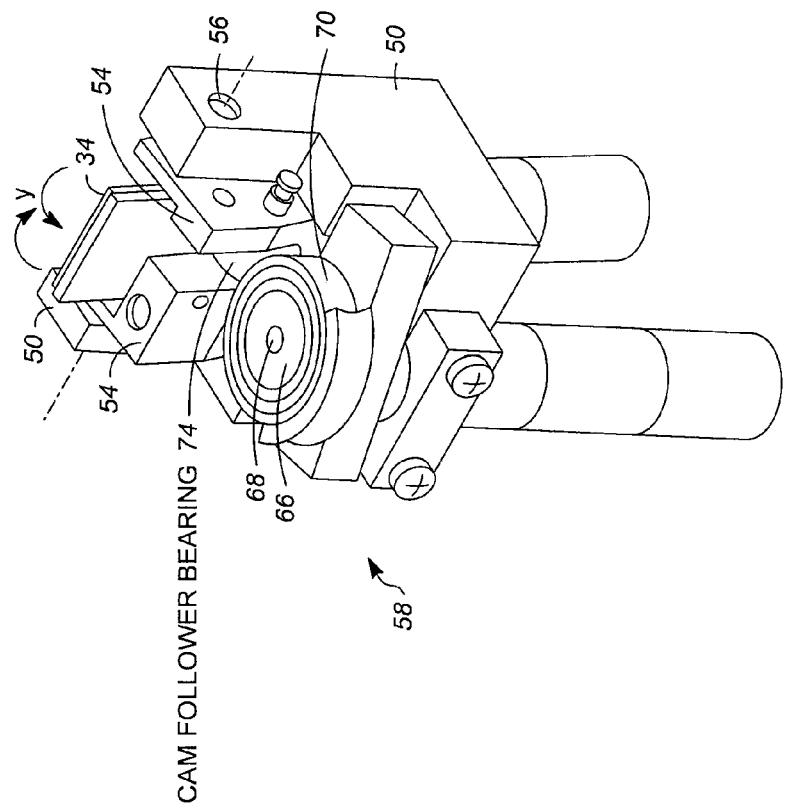
FIG. 6A is a rear perspective view of the X,Y scanning assembly of the treatment apparatus of FIG. 1A.

Components of the scanner 20 are shown in FIGS. 6A and 6B. Scanner includes a base 50 fixed within the handpiece. Base 50 is a u-shaped piece defining an opening 52. A yoke 54 is mounted within the opening 52. Yoke 54 is mounted to the base by pins 56 and is pivotable about the pins to produce y-direction movement of the mirror. Mirror mount 46, which carries mirror 34, is coupled to the yoke 54.

Y-movement scanning unit 58 is mounted to the base 50. X-movement scanning unit 60 is mounted to the yoke 54.

In general, the y-movement scanning unit 58 has components that abut the yoke 54 to produce forward/backward pivoting of yoke 54 about pins 56, causing corresponding movement of mount 46 and mirror 34. See the arrows marked "y". The x-movement scanning unit pivots the mount 46 back and forth as indicated by arrows "x" to produce side to side movement of the mirror 34.

Figure 7B:
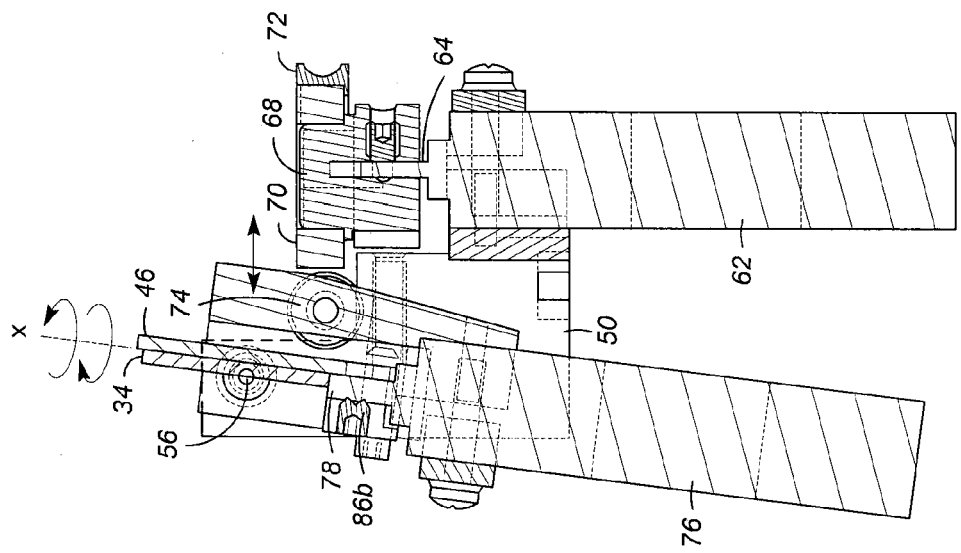
FIG. 7B is a cross-sectional side elevation view of the scanning assembly of FIG. 6A.
Figure 7A:
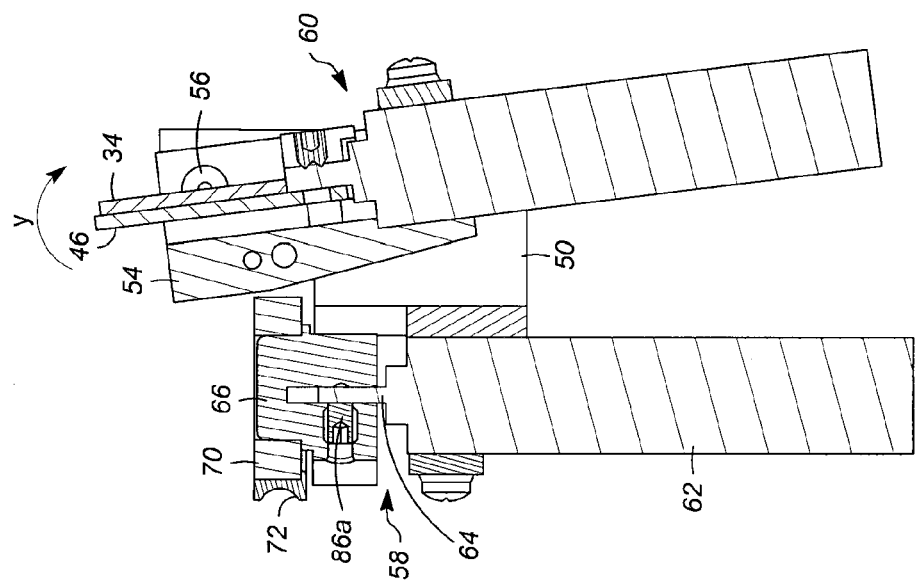
FIG. 7A is a cross-sectional side elevation view of the scanning assembly of FIG. 6A.

Details of the Y-movement scanning unit 58 will be described with reference to FIGS. 7A through 7B. The unit 58 includes a stepper motor 62 that produces rotation of shaft 64. A cam 66 having a central mount 68 is coupled to the shaft 64. Cam 66 includes a cam bearing 70 and a spring saddle 72. Cam bearing 70 is positioned in contact with a cam follower bearing 74 (FIGS. 6A and 7B) on the yoke 54.

The cam 66 and shaft 64 are coupled such that the mount 68 is laterally offset from the shaft 64. Thus, activation of the motor to rotate the shaft 64 produces eccentric rotation of the cam. A useful way to visualize the movement of the cam is to picture an automobile wheel being rotated about an axel that is laterally offset from the center of the wheel. The eccentric movement of the cam 66 results in cyclic movement of the cam bearing 70 towards and away from the cam follower bearing 74 with which the cam bearing 70 is in contact. As a result, the yoke 54 (as well as all components carried by the yoke) pivots back and forth about the pins 56, moving the mirror 34 as indicated by arrows "y" in FIGS. 6A and 7A. Spring saddle 72 aids in maintaining contact between the cam follower bearing 74 and the cam bearing 70 throughout scanning.

X-axis scanning unit 60 includes a stepper motor 76 carried by the yoke 54. Stepper motor 76 includes a shaft 78 coupled to the mirror mount 46. Activation of the motor 76 pivots the mirror 34 side to side relative to the axis of the shaft 78.

Each of the stepper motors 62, 76 is preferably provided with an anti-backlash spring 86a, 86b coupled to its shaft, to prevent backlash of the shaft when the polarity of the input to the motor is reversed.

Figure 8:
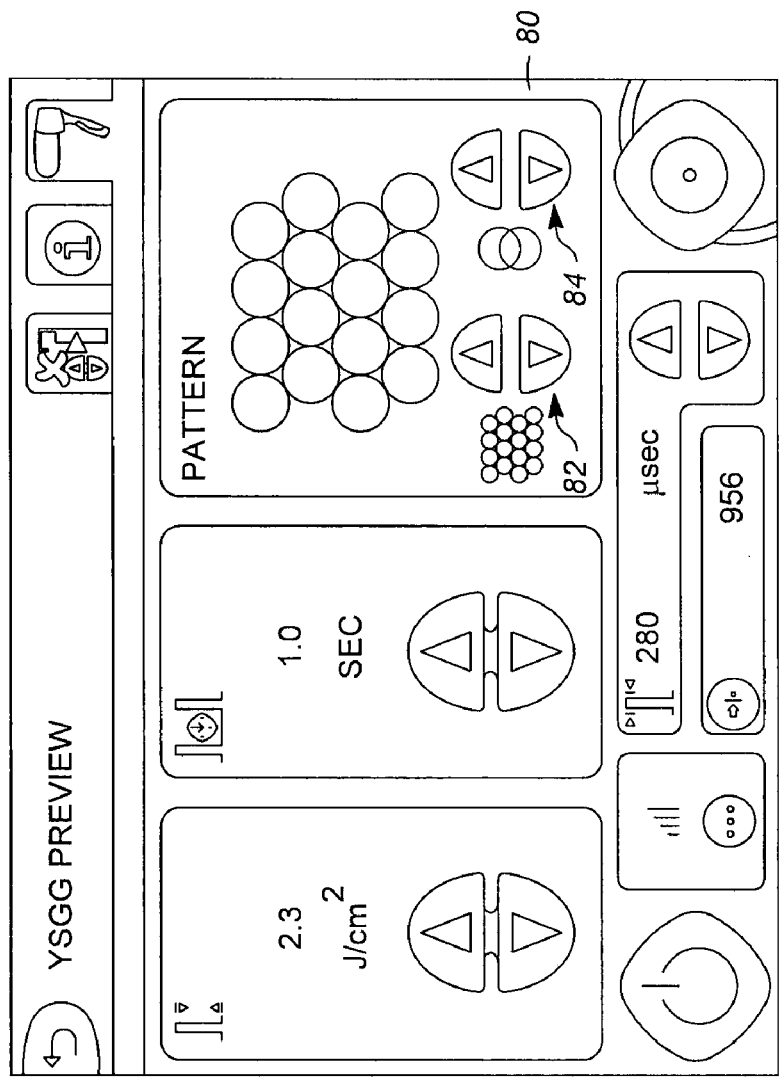
FIG. 8 is an exemplary control panel for the console of the treatment apparatus of FIG. 1A.

Referring to FIG. 8, the console may include a user interface 80 allowing a user to select one or more treatment parameters. For example, a user might have the option to scroll through and select from a menu of available treatment patterns using pattern select keys 82. Similarly, the degree by which spots in the treatment pattern overlap or are spaced apart may be selected using overlap/spacing keys 84. A selected pattern/spacing may produce distinct spaced-apart treatment spots, or overlapped spots, or a continuous "painting" of the skin surface. Other input keys may be used to select pulse width, fluence, pulse duration etc.

In an exemplary embodiment, operational and treatment parameters might, but are not limited to, the following:

Wavelength: 2790 nm

Output power: up to 20 W

Pulse Energy: Up to 1 J per pulse

Pulse Duration: 100-600 μsec

Repetition Rate: Up to 20 Hz

Spot Size: Approx 5 mm

Maximum Pattern Size: 3 cm×3 cm

Treatment fluence range approx 2-5 J/cm$^2$

Ablation depth: 20-50 μm

Subsequent damage (e.g. coagulation depth): additional 30-50 μm beyond the ablation depth.

During use of the disclosed treatment apparatus, the user selects the appropriate treatment parameters. Next, the handpiece 12 (FIG. 2) is positioned such that the distance guide 38 is in contact with the skin of a patient. With the distance guide in contact with the skin, the laser is activated such as by depressing a footswitch. The user maintains the handpiece position while the scanner steps the treatment beam in the X and Y directions as discussed to create the desired treatment pattern.

Figure 9:
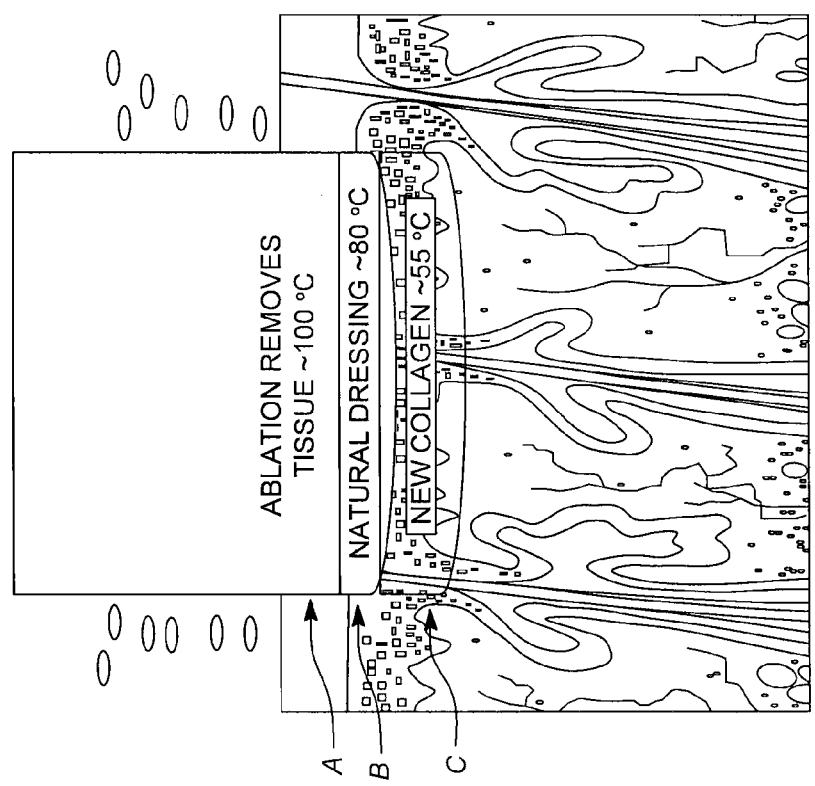
FIG. 9 schematically illustrates the coagulative and ablative effects of the treatment apparatus of FIG. 1A on skin tissue.

As illustrated in FIG. 9, skin treatment using the disclosed laser operating at a wavelength of 2.79 μm allows three effects to be achieved. First, application of the treatment beam ablates approximately 20-50 μm, and preferably approximately 30-50 μm, of the epidermis (region A in FIG. 9) at a temperature in the range of approximately greater than 90° C., and more preferably greater than approximately 100° C. Residual heat (in the range of approximately 70-90° C. and preferably approximately 80° C.) coagulates an additional 30-50μ of the epidermis (region B), creating a natural dressing for the skin. This natural dressing peels from the skin in approximately 3-5 days. The residual heat raises the temperature of a portion of the dermis (region C) to a temperature in the range of approximately 45-65° C. (and preferably approximately 55° C.), which promotes generation of new collagen within the dermis.

The disclosed apparatus and associated methods have been described in connection with resurfacing and/or rejuvenating skin for treatment of dermatological conditions such as improvement of facial texture by eliminating fine lines, wrinkles, and/or scars, or for eliminating discoloration caused by photo damage. However, the method and apparatus may also be used to treat for other applications and/or to treat other biological tissue.

While various embodiments have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Additionally, it is contemplated that the features of the various disclosed embodiments may be combined in various ways to produce numerous additional embodiments. Thus, the present invention should not be limited by any of the above-described exemplary embodiments, but should be defined only in accordance with the following claims and their equivalents.

Any and all patents, patent applications and printed publications referred to above, including those relied upon for purposes of priority, are incorporated by reference.

We claim:

1. A method for reducing skin wrinkles comprising the steps of:

generating a pulsed beam of laser radiation from a YSGG gain medium, said beam of radiation having a wavelength of 2.79 microns; and scanning the pulsed beam over the skin in a two dimensional array of spots within a treatment region, with the fluence at each spot being between 2 and 5 joules/cm2 and with the pulse width being between 100 and 600 microseconds and wherein the fluence and pulse width are selected to ablate the upper surface of the skin to a predetermined depth and to create a layer of coagulated tissue below the ablated region with the thickness of the layer of coagulated tissue being at least as great as said predetermined depth of ablation and wherein the temperature of the skin to be ablated is raised to at least 90 degrees centigrade while the tissue in the layer to be coagulated is raised to a temperature between 70 and 90 degrees centigrade and wherein said coagulated tissue creates a natural dressing which subsequently peels from the skin resulting in a reduction in skin wrinkles.

2. A method as recited in claim 1, wherein the fluence and the pulse width of the radiation are selected so that the thickness of the layer of coagulated tissue is between 30 and 50 microns.

3. A method as recited in claim 2, wherein the fluence and the pulse width of the radiation are selected so that the predetermined depth of ablation is between 20 and 50 microns.

4. A method as recited in claim 1, wherein the fluence and pulse width are selected to heat the skin below the coagulation layer to a temperature between 45 and 65 degrees centigrade to promote the generation of new collagen below the coagulation layer.

5. A method as recited in claim 1, wherein the beam is scanned in a manner so that the spots overlap.

6. A method for reducing skin wrinkles comprising the steps of:

generating a pulsed beam of laser radiation from a YSGG gain medium, said beam of radiation having a wavelength of 2.79 microns; and scanning the pulsed beam over the skin in a two dimensional array of spots within a treatment region, with the fluence at each spot being between 2 and 5 joules/cm2 and with the pulse width being between 100 and 600 microseconds and wherein the fluence and pulse width are selected to ablate the upper surface of the skin to a predetermined depth and to create a layer of coagulated tissue below the ablated region with the thickness of the layer of coagulated tissue being at least as great as said predetermined depth of ablation, said coagulated tissue creating a natural dressing which subsequently peels from the skin resulting in a reduction in skin wrinkles and wherein the fluence and pulse width are selected to heat the skin below the coagulation layer to a temperature between 45 and 65 degrees centigrade to promote the generation of new collagen below the coagulation layer.

7. A method as recited in claim 6, wherein the temperature of the skin to be ablated is raised to at least 90 degrees centigrade while the tissue in the layer to be coagulated is raised to a temperature between 70 and 90 degrees centigrade.

8. A method as recited in claim 6, wherein the fluence and the pulse width of the radiation are selected so that the thickness of the layer of coagulated tissue is between 30 and 50 microns.

9. A method as recited in claim 8, wherein the fluence and the pulse width of the radiation are selected so that the predetermined depth of ablation is between 20 and 50 microns.

10. A method as recited in claim 6, wherein the beam is scanned in a manner so that the spots overlap.

* * * * *